(12) United States Patent
Fahl (10) Patent No.: US 10,188,817 B2
(45) Date of Patent: Jan. 29, 2019

(54) SPEAKING VALVE

(71) Applicant: Andreas Fahl Medizintechnik—Vertrieb GmbH, Cologne (DE)

(72) Inventor: Andreas Fahl, Köln (DE)

(73) Assignee: Andreas Fahl Medizintechnik—Vertrieb GmbH, Cologne (DE)

( * ) Notice: Subject to any disclaimer, the term of this patent is extended or adjusted under 35 U.S.C. 154(b) by 897 days.

(21) Appl. No.: 14/740,382

(22) Filed: Jun. 16, 2015

(65) Prior Publication Data
US 2015/0273168 A1 Oct. 1, 2015

Related U.S. Application Data

(63) Continuation of application No. PCT/EP2013/003790, filed on Dec. 16, 2013.

(30) Foreign Application Priority Data

Dec. 19, 2012 (DE) .................. 10 2012 024 817

(51) Int. Cl.
| | |
|---|---|
| *A61M 16/04* | (2006.01) |
| *A61M 16/10* | (2006.01) |
| *A61F 2/20* | (2006.01) |

(52) U.S. Cl.
CPC .......... *A61M 16/0468* (2013.01); *A61F 2/20* (2013.01); *A61M 16/047* (2013.01);
(Continued)

(58) Field of Classification Search
CPC .......... A61M 16/0465; A61M 16/0468; A61M 16/047; A61M 2205/75; A61M 2210/1032; A61F 2/20; A61F 2/203; A61F 2002/206
(Continued)

(56) References Cited

U.S. PATENT DOCUMENTS

| | | | | |
|---|---|---|---|---|
| 5,806,515 A | * | 9/1998 | Bare | A61F 2/203 128/207.15 |
| 2004/0089291 A1 | * | 5/2004 | Persson | A61M 16/0468 128/200.16 |

(Continued)

FOREIGN PATENT DOCUMENTS

| | | | | |
|---|---|---|---|---|
| DE | 102005007234 B3 | * | 7/2006 | ............ A61M 16/04 |
| DE | 202011003781 U1 | * | 5/2011 | ........ A61M 16/0468 |
| EP | 1747792 A1 | * | 1/2007 | ........ A61M 16/0468 |

OTHER PUBLICATIONS

Machine translation of DE 202011003781 U1.*
International Search Report for PCT/EP2013/003790.*

*Primary Examiner* — (Jackie) Tan-Uyen T Ho
*Assistant Examiner* — Joseph D Boecker
(74) *Attorney, Agent, or Firm* — Dinsmore & Shohl LLP (57) ABSTRACT

The invention relates to a speaking valve for laryngectomized and tracheotomized persons that is easy and economical to produce. According to the invention, the speaking valve comprises a proximal first opening and a distal second opening, a filter, which is at least partially surrounded by the housing, which filter is made of an elastic material, and has a proximal first end and a distal second end, wherein the filter partially protrudes beyond an end face of the housing at the distal second opening, and wherein a cover is connected by means of at least one partial region of the bottom surface thereof to a top side of the filter at the distal second end of the filter. A diameter $d_1$ of the cover is greater than a diameter $d_2$ of the filter, such that an edge projecting beyond a lateral filter wall of the filter is formed, wherein by application of pressure to the cover from an initial position, a bottom surface of the edge at least partially interacts with the end face of the housing in order to produce a closed position of the speaking valve, and wherein the cover (Continued)

together with the filter returns to the initial position when unloaded.

13 Claims, 4 Drawing Sheets

(52) U.S. Cl.
CPC ..... *A61M 16/105* (2013.01); *A61F 2002/206* (2013.01); *A61M 2205/75* (2013.01)

(58) Field of Classification Search
USPC ............................................ 251/18, 84, 170
See application file for complete search history.

(56) References Cited

U.S. PATENT DOCUMENTS

| | | | | |
|---|---|---|---|---|
| 2008/0142013 | A1* | 6/2008 | Hallett ................... | A61M 16/06 128/205.24 |
| 2010/0288284 | A1* | 11/2010 | Persson ............. | A61M 16/0468 128/207.14 |
| 2011/0220108 | A1* | 9/2011 | Persson ............. | A61M 16/0468 128/205.29 |
| 2013/0239958 | A1* | 9/2013 | Persson ............... | A61M 16/047 128/201.13 |
| 2014/0150779 | A1* | 6/2014 | Persson ............. | A61M 16/1055 128/201.13 |
| 2015/0238718 | A1* | 8/2015 | Schnell ..................... | A61F 2/20 128/202.27 |

* cited by examiner

SPEAKING VALVE

CROSS-REFERENCE TO RELATED APPLICATIONS

This application is a continuation of PCT/EP2013/003790 filed Dec. 16, 2013, which claims priority of German Application DE 10 2012 024 817.2 filed Dec. 19, 2012.

FIELD OF THE INVENTION

The present invention relates to a speaking valve for laryngectomized and tracheotomized persons with a housing.

BACKGROUND OF THE INVENTION

During surgical procedures in the upper respiratory tract, it may be necessary to insert an artificial breathing opening (tracheostoma) into the trachea, so that by means of a bypassing of the oral cavity and voice box, air can be directly breathed into the lungs. Generally filter systems are used for laryngectomized and tracheotomized persons, which consists of a plaster with an inserted filter, a usually self-adhesive baseplate or a tracheal cannily—which is generally made of a plastic material-, into which filters of various kinds can be inserted. Filter systems, which are used for laryngo-tracheal aids such as tracheal cannulas and plasters- or baseplates, include the so-called humidity and heat exchangers, which are also called artificial noses. The purpose of these is to reproduce the missing regulation mechanisms for warming and moisturizing the breath for tracheotomized, but also for laryngectomized patients and to prevent a direct contact of the trachea with dry, cold and unfiltered air. The irritation that is caused hereby leads to an increased mucus production with the associated danger of incrusting. By means of humidity and heat exchangers, the breathed-in air is being moisturized, warmed and filtered at the same time. In this way the before-mentioned extended incrusting is prevented to a large extend. A regular wearing of the artificial nose helps particularly when there is an intense discharge of secretion, since the moisturizing of the mucous membranes in the trachea reduces the production of secretions. Humidity and heat exchangers can further be equipped with a speaking function and they are then referred to as speaking valves, as in the case of the present invention, whereas other terms such as e.g. vocal valves are also customary.

Generic speaking valves are widely known from the prior art. Likewise, DE 699 20 440 T2 presents a generic device, which is referred to as a vocal valve with filter, whereby the vocal valve serves as a connection with a tracheostoma, and it features a regenerative filter for humidity and heat exchange during breathing by means of the vocal valve, as well as a housing, which holds the filter, and a first opening on one side of the filter in order to connect to the tracheostoma as well as at least one second opening on an opposite side of the filter, which is connected to the environment, and a manually operable valve element in order to block the airflow through the filter, whereby a tube reaches into the inner of the housing and forms a valve seat which defines the first opening, in order to accomplish a sealed connection with the valve element by means of a manual actuation of it. The vocal valve which is presented there is fairly complex in its construction and uses a spring as resetting mechanism or a deformable cover element as valve element.

SUMMARY OF THE INVENTION

It is thus the objective of the present invention to present a speaking valve for laryngectomized and tracheotomized persons that is constructed in a simple way.

This objective is realized by means of a speaking valve according to the invention for laryngectomized and tracheotomized persons with a housing that comprises a proximal first opening and a distal second opening, a filter that is at least partially surrounded by the housing, which filter is made of an elastic material, and with a proximal first end and a distal second end, wherein the filter partially protrudes beyond an end face of the housing at the distal second opening, and wherein at least a partial section of a the lower surface of a cover is preferably connected to an upper side of the filter at its distal second end, preferably solidly connected, whereby a diameter $d_1$ of the cover is greater than a diameter $d_2$ of the filter, so that an edge projecting beyond a lateral filter wall is formed, wherein by application of pressure onto the cover from an initial position, a bottom surface of the edge at least partially interacts with the end face of the housing in order to produce a closed position of the speaking valve, and wherein the cover together with the filter returns to the initial position when unloaded. In particular the edge of the cover at its lower surface, which is projecting beyond the lateral filter wall, is formed in a ring-shape all around. This projecting of the filter beyond the end face of the housing should be preferably within the range of approx. 5% to approx. 50%, preferably approx. 8% to approx. 30%, further preferably approx. 10% to approx. 20% of the overall height of the filter, whereby the overall height is determined in the non-compressed state of the filter, starting from the lower surface at its proximal first end towards the upper surface which defines the distal second end.

The term "proximal end" or "proximal opening" in the sense of the present invention describes the end or the opening that is facing towards the center of the body of the one using the speaking valve according to the invention, whereas the term "distal end" or "distal opening" in the sense of the present invention describes the end or the opening of the housing or of the filter that is facing away of the center of the body of the one using it.

The speaking valve according to the invention features the great advantage, that it can be produced in a particularly simple way and that it is thus very cost-effective. At the same time, it is possible that the one using it can produce a speaking in a simple way by closing the speaking valve by means of applying pressure onto the cover from an initial position into a closed position. The filter thus serves the purpose of filtering and moisturizing the breathing air as well as of an elastic means, by means of which the speaking valve can return from the closed position into the initial position. The elastic material is hereby preferably made from a synthetic material, whereby it is further preferred that the synthetic material features a sponge-like structure with a plurality of pores and channels, wherein these are preferably not arranged in any particularly arranged way. But it is possible that additionally or individually arranged and aligned channels are designed into the filter body itself.

The air reaches into the filter at least through one outer wall of the filter in the area between the end face of the housing and the lower surface of the edge of the cover and is then redirected towards the distal opening of the housing or towards the distal end of the filter. Breathed-out air travels in the opposite way through the filter of the speaking valve according to the invention. But it is also possible that air passes through at least one central opening in the cover without being redirected.

The filter is preferably solidly attached to the cover. The transfer into a closed position is exclusively done via the cover, whereby a compression of the filter is performed at the same time. In the section that protrudes beyond the end face, the filter is solely guided by the cover. Consequently, the cover is not only touching the filter. Otherwise it would loosen and a closing of the speaking valve would hardly be possible anymore.

Between the housing and the cover, on the outside of the filter body, it is possible to arrange at least one, preferably at least two, three, four, five, six or more elastic elements, which are attached to the cover and/or to the housing, in particular within the area between the distal end face of the housing and the edge that is formed on the lower surface of the cover, e.g. in the shape of elastic rubber bands, which twist towards the outside during the transfer into a closed position, and which move the filter back from the closed position into its initial (open) state when it is released, thus supporting the filter. But it is preferred that the speaking valve according to the invention does not consist of any connections between the housing and the cover. In this way, the compressing and guiding of the filter is solely done via the cover, which is solidly attached to the filter. Consequently, the filter does not get any additional guiding in the section which is protruding beyond the end face, the guiding is solely accomplished by means of the cover. In a further preferred embodiment, a protective element can be arranged in the area of the distal second opening, which at least partially protects the part of the filter which is protruding beyond the end face in the section of its outer wall. Thereby, the protective element can be preferably arranged on an outer wall of the housing, or further preferred on the distal end section of it. It is preferred that the protective element consists of at least one opening in order to enable the passage of air through the outer surface of the filter. Advantageously it is designed in ring-shape with a lower ring portion that is preferably arranged in a solid manner on the outer wall of the housing, and an upper ring portion, which is arranged in the section of the outer wall of the filter and consequently on the top, but not above the distal end face of the housing. The upper surface of the upper ring portion is arranged at least slightly below the distal second end of the filter. The lower and the upper ring portion are preferably connected by means of two connecting bars, between which openings are arranged in order that air can pass through. The lower and/or the upper ring portion have an inner diameter, which is only slightly larger than the diameter $d_1$ of the cover. The protective element is not connected to the cover. It does not provide any guiding support to the filter when the speaking valve is transferred into a closed position. The protective element as well as the elastic elements prevent a random closing of the speaking valve, in particular while sleeping.

A synthetic material is preferably used for the elastic material for the filter, which is chosen from a group consisting of polyurethane, preferably from the group of polyurethane soft foams. The synthetic material is preferably made of foam material, preferably with a cell count of 5.5 to 7.5 (1/cm). The gross density of the foam material preferably ranges between 20 and 26 kg/m$^3$, when measured according to DIN EN ISO 845. The compression strength CV40 according to DIN EN ISO 3386-1 preferably ranges between approx. 2.9 and approx. 5 kPa for the foam. The tensile strength according to DIN 53571 A for the foam preferably lies within a range of approx. 55 and approx. 200 kPa, preferably is should be at least 58 kPa. The elongation at break according to DIN 53571 A for the foam amounts to at least 90%, preferably it lies within a range on approx. 95% and approx. 200%.

Advantageously, the filter is held by some means for fastening on the inside wall of the housing, this fixing aid being preferably arranged at some distance to the proximal first opening of the housing. Advantageously, the fixing aid is at least partially arranged as a circulating flange, in the shape of a ridge and/or in a way of a ledge that is reducing particularly towards the center of the housing. In the sense of the preset invention, the term ridge-shaped includes e.g. star-shaped formations, such as e.g. three-, four-, five-, six-, or eight-armed star-formations as well, wherein each arm is formed by one ridge. Preferably, the proximal surface of the filter is arranged at some distance to the proximal first opening of the housing. In this way it is possible to use a filter with a low construction height. Especially by means of the protruding beyond the end face of the housing, due to the enlarged usable surface, it is possible that the filter can fulfill its heat and humidity exchanger function even though there is a volume reduction.

The filter is advantageously attached to the fixing aid by means of adhesion, welding or hooking. For a ridge-shaped embodiment in form of a cross with four arms (ridges), it could for example be possible to position that cross near or at the end face of the proximal first opening of the housing of the speaking valve according to the invention, and the filter with its lower proximal end or lower surface, which is facing towards the proximal first opening, could be attached to the surface of the cross, which is facing towards this surface of the filter by means of adhesion. But it could also be intended, that fixing aids are designed e.g. in a circumferential manner all around the inner wall, be it near the proximal opening of the housing, or be it at some distance to it, e.g. in form of a circumferential edge, in a ridge-shaped manner, including star-shapes of any kind, and/or in form of a ledge, which is extending towards the inside of the housing, while particularly getting thinner. These can then be arranged individually or in addition to a further fixing aid at the proximal opening of the housing, e.g. a ridge, including one that is arranged in star-shaped. If the fixing aids are designed in form of a ledge, which is extending towards the inside of the housing, while getting thinner, they are preferably arranged in a cone-shaped way, so that they can reach into the elastic material of the filter. Advantageously, at least two, three, four, five, six or eight of suchlike fixing aids are arranged on the inner wall of the housing that reach into the elastic material of the filter, preferably equally distributed around the inner wall, further preferred in one common layer.

The at least partially circulating edge can also feature interruptions, so that by means of its upper surface, which is facing towards the proximal end of the filter, a supporting surface is provided for the filter which is on one level. It is e.g. possible that two, three, four or more circular arc-shaped ring-sections are intended in one layer on the inner wall of the housing. When these circular arc-shaped ring-sections are connected by means of enlarging these, a circular edge is produced. The filter is resting on this at least partially circular edge. It is possible to put e.g. glue on the surface of the circular edge that is facing towards the proximal end of the filter, which provides a connection to the elastic material of the filter, or it is also possible that a welding with the filter material is performed there. It is also possible that the filter material is hooked and held by an array of hooks, which reach into the filter material on the surface of the at least partially circular edge that is facing towards the proximal end of the filter. The at least partially circular edge is preferably arranged near the proximal edge of the housing and it is possible that it, including the surface that is arranged in star-shape and that faces away from the housing can—just like the ridges—be at flush with the lower proximal end surface of the housing.

In the sense of then present invention it is advantageous that the housing consists of an air permeable bottom part that is arranged at the proximal first end. The bottom part can hereby be a fixing aid in the above mentioned way, in particular if it is designed at least partially as a circumferential edge or also in ridge-shape or star-shape.

In a preferred embodiment of the present invention, the cover is attached to the filter in a solid or detachable manner, preferably solid. Advantageously, the cover and the filter are glued, welded or hooked together, it is especially preferred if they are glued. The gluing does not have to be done on the entire distal surface of the filter, it can much rather also be done on only a partial section, the same applies to the welding or the hooking.

Advantageously, it is intended that the edge that is arranged on the lower side of the cover, which is outside of the outer circumference area of the filter, is arranged in a ring-shape and that it covers at least the end face of the distal opening of the housing, further preferred is that it would protrude slightly over it, which would be beyond the outer contour of the housing, formed by the circumference area of it. At max, this protrusion would amount to double the width of the ring-shaped end face of the distal opening of the housing, and it preferably lies within the range of the 1.1-fold and approx. the 1.9-fold width of the end face of the distal opening of the housing.

In a preferred embodiment, at least one enlarging aid is arranged at one outer wall of the housing. It is especially preferred that the enlarging aid is made in form of a flange, preferably a circular flange. But the enlarging aid can also be designed in form of an interrupted flange, so that in this case, several enlarging aids are arranged on the outer wall of the housing for the cover. The enlarging aid is advantageously arranged on the outer wall of the housing in such a way that a distal surface, or a surface that is facing away from the body is at flush with the end face of the housing. By means of this enlargement, the support- or contact surfaces of the housing for the cover are extended, which improves an interruption of the air stream by means of touching on the lower surface of the ring-shaped edge that is arranged on the cover.

In a preferred embodiment, an outer contour of the lower surface of the edge of the cover and an outer contour of the end face of the housing and/or of the enlarging aid are adapted in such a way on the outer wall of the housing that they fit into each other. This can be e.g. accomplished if the lower surface of the edge and the end face of the housing and/or the enlarging aids feature surfaces that are arranged parallel and plane towards each other. But an embodiment with another outer contour of the lower surface of the edge and of the end face of the housing and/or of the enlarging aid is also possible. By means of adapting of the shape of the outer contour of the lower surface of the edge and that of the end face of the housing, it is possible to improve the operating of the speaking valve according to the invention in an advantageous way. Thus, a centering of the cover in closed position can be accomplished by means of the mentioned adaption, so that a generally possible movement of the cover along with its connected filter in a direction that is parallel to the end face of the housing is prevented. By means of such a movement as was mentioned before, a shifting of the ring-shaped edge of the cover to such an extent, that it would no longer work together with the end face of the housing at least in a partial section, is prevented.

In a preferred embodiment, a first elevation is arranged on the end face and/or on the enlarging aid on the outer wall of the housing. The elevation can also be arranged partially on the end face and partially on the enlarging aid on the outer wall of the housing. The first elevation can feature any desired formation. It is e.g. possible that the enlarging aid in one embodiment, which is arranged on the outer wall of the housing, is arranged at least partially as a circular flange, whereby its distal surface, that means the surface that is facing towards the cover, is not at flush with the end face of the housing, but rather protrudes beyond it into the direction towards the cover. It is possible that the elevation can feature different kinds of contours when viewed in cross section through a plane that is perpendicular to it. It can e.g. be designed in a rectangular way, or with an slant on one side, preferably the side facing towards the inside of the housing, but it could also be formed by means of circular arcs at least to some extend on the side facing towards the inside of the housing, and thereby feature a surface with a sigmoidal shape.

In a further preferred embodiment, a second elevation is arranged on a lower surface of the edge of the cover. This second elevation is preferably arranged on the lower surface of the ring-shaped edge of the cover, which interacts with the end face and/or the at least one enlarging aid that is arranged on an outer wall of the housing. This second elevation can hereby be adapted to the first elevation in its outer contour, which is arranged on the end face and/or the enlarging aid of the housing, and features e.g. a rectangular shape when viewed in cross section of a plane that runs perpendicular through the second elevation and a plane with the center axis running through the housing, whereby it is preferably also possible that a surface of the elevation that is assigned to the first elevation of the housing can feature a slant. The surface of the second elevation can also be at least partially designed by means of circular arcs, and feature e.g. a surface with a sigmoidal shape.

In the sense of the present invention, an adaption of the outer contour of the lower surface of the edge of the cover towards the outer contour of the end face of the housing can also be accomplished in such a way, that the end face is designed with a slant towards the inside of the housing, that is, without any first elevation, so that a correspondingly shaped (second) elevation, which is arranged on the lower surface of the ring-shaped edge of the cover, and which is adapted in its outer contour to the slanting of the end face of the housing towards the inside of the housing, can interact with it. With such a formation, the end face does not feature any elevations, but rather a recess or a gap, which interacts with the (second) elevation on the lower surface of the ring-shaped edge of the cover.

In a particularly preferred embodiment of the present invention, at least one centering aid is arranged on the lower surface of the edge of the cover and/or of the end face or on the at least one enlarging aid of the housing. The at least one centering aid is hereby arranged on the lower surface of the ring-shaped edge of the cover, which is located outside of the outer circumference or -wall of the filter. Just like the adaption of the outer contour of the lower surface of the edge of the cover towards the outer contour of the end face of the housing, the centering aid also serves the purpose of an improved handling of the speaking valve according to the invention. A first centering aid is e.g. formed in a pin-shaped way and it is arranged on the lower surface of the ring-shaped edge. It is hereby preferably intended, that several of such pin-like centering aids are arranged on the lower surface of the ring-shaped edge of the cover, e.g. at least two, three, four, five, six, eight or more. When viewed in cross section, the pin-like centering aid can feature any desired geometrical shape, and in the simples case it is formed in a rectangular shape in cross section, but it can also be formed in a triangular shape in cross section, and can possibly also be formed as a cone. This at least one centering aid can engage e.g. with at least one second centering aid, which is arranged on the end face of the housing and/or in the area of the enlarging aid that is arranged on the outer wall of the housing. In this case, it is e.g. possible that the housing wall—starting from the distal end face—advantageously features recesses as a second centering aid, which are adapted to the outer contour of the first centering aid. But it is also possible that such corresponding recesses are arranged e.g. within the enlarging aid, which is arranged on the outer wall of the housing. Hereby the recess or gap that forms the second centering aid, can accommodate the first centering aid fully, or also only partially. In the latter case, the second centering aid is to be approached as a gap, which is arranged e.g. in the area of the inner wall of the enlarging aid, facing towards the inside of the housing, or also in the area of the inner wall of the housing, facing towards the inside of the housing, and it is arranged starting from the distal end face of it. When the second centering aid fully accommodates the first centering aid, the second centering aid is to be approached as a borehole or recess.

In a further preferred embodiment, at least a partial sealing gasket is to be arranged on the lower surface of the edge, in particular on the lower surface of the ring-shaped edge of the cover, and/or the end face or the at least one enlarging aid. But it is also possible that the sealing gasket is arranged on the first and/or second elevation, which is on the end face and/or the enlarging aid that is arranged on the outer wall of the housing, or on the lower surface of the edge of the cover or on the second elevation which is located there.

The sealing gasket can be made of any suitable material that is medically harmless, e.g. of a suitable silicone material or the like.

Advantageously, the sealing gasket is produced in one piece together with the housing or cover, which means that it is tightly connected to the housing or cover, possibly also in a way that it can be loosened. The connection can advantageously be done by means of gluing, but also by means of coextrusion or by other types of connection.

BRIEF DESCRIPTION OF THE DRAWINGS

These and other advantages of the present invention are explained in more detail by means of the following figures. It is shown.

DETAILED DESCRIPTION OF THE PREFERRED EMBODIMENTS

Figure 1:
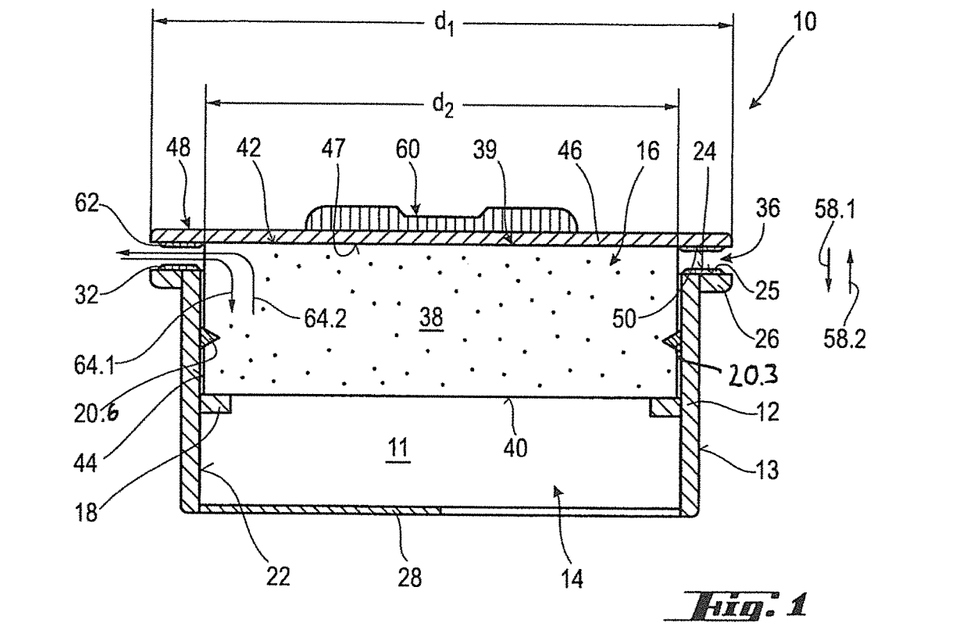
FIG. 1: a cross section according to cut A-A according to FIG. 3 through a first embodiment of the speaking valve according to the invention in initial position.

FIG. 1 depicts an overall speaking valve for laryngectomized and tracheotomized persons according to the invention with the reference sign 10 with a housing 12, which can be attached to a retainer (not depicted), like e.g. a baseplate or a plaster that can be worn on the neck of the patient, or to a trachea cannula. The housing 12 consists of an outer wall 13 as well as a proximal first opening 14, which is arranged in close proximity to the body of the patient, and a distal second opening 16, which is arranged facing away from the body with reference to the patient. For the most part, a filter 38 is arranged inside of housing 12, with a side wall 44 that is made of an open-pored synthetic material, which is made in an elastic manner. Housing 12 features a distal end face 24. On the outer wall 13, in the area of the distal second opening 16 of housing 12, an enlarging aid 26 is arranged in form of a circulating flange. The surface 25 of this flange is arranged at flush with the end face 24 of housing 12.

On one inner wall 22 of housing 12, a fixing aid 18 is arranged that is formed as a circular flange, whereby the distal upper surface of it can come or does come in contact with a proximal surface 40 of filter 38. Furthermore, a total of six additional fixing aids 20.1 to 20.6 (see FIG. 3) are arranged on the inner wall 22 of housing 12, which are formed in a cone-shaped way and which reach into the elastic material of filter 38 with their pointed ends. These additional fixing aids 20 are distributed equally along the inner wall 22 of housing 12, and are aligned within one plane that is perpendicular to an imaginary center axis of the filter and approx. parallel to e.g. the proximal surface 40 of filter 38. Advantageously, at least two further, preferably three, more preferably four, five, six or eight or more of such fixing aids 20 are arranged on the inner wall 22 of housing 12. These further fixing aids 20 prevent that filter 38 can slip out of an inner compartment 11 of housing 12. Alternatively and in the sense of the present invention, it can also be intended that further fixing aids 20 are left out, and that fixing aid 18 is instead equipped e.g. with hook-like means on its distal surface or that at least partially, but preferably on the entire surface, an adhesive is applied, which provides or produces a tight connection with the elastic material of filter 38. In this way, a slipping of filter 38 out of the inner compartment 11 is prevented.

Figure 3:
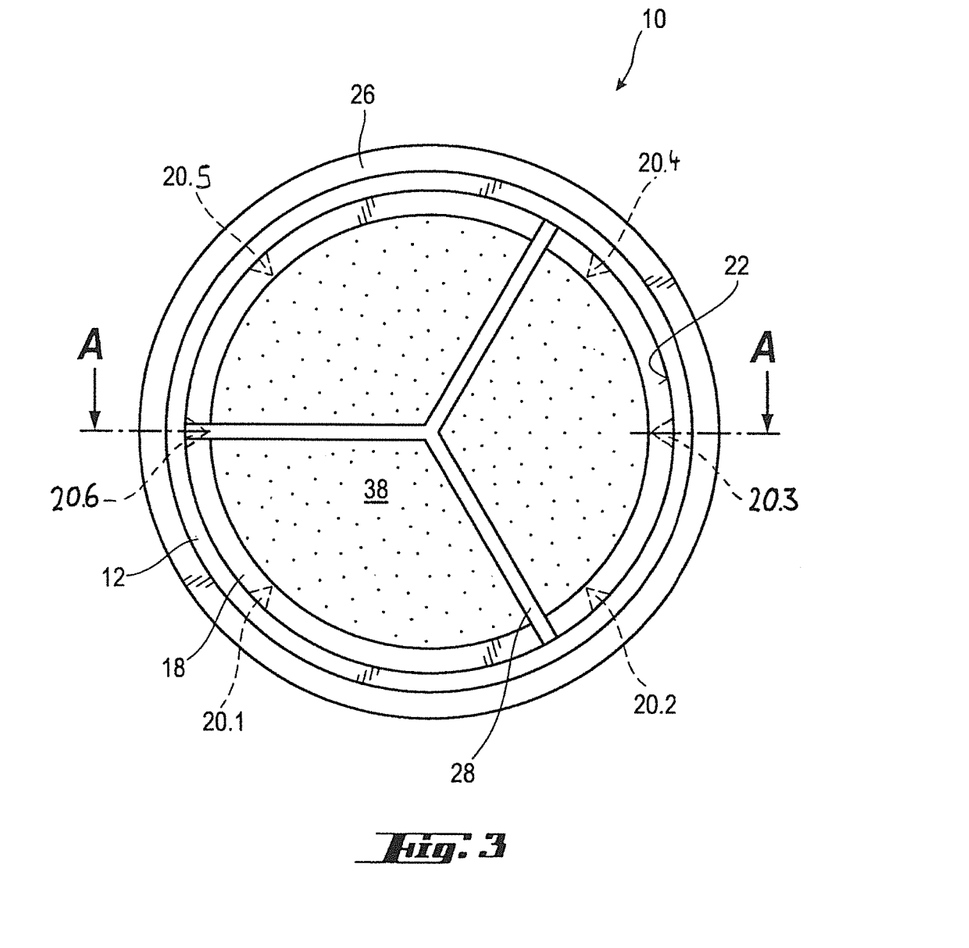
FIG. 3: a bottom view of the first embodiment of the speaking valve according to the invention according to FIG. 1.

Housing 12 further consists of a bottom part 28, which can be arranged in star-shape with three arms, as it can be derived from FIG. 3. The ridges of the bottom part 28 connect to the inner wall 22 of housing 12. Advantageously, a proximal surface of bottom part 28 is arranged approximately at flush with a proximal end face of housing 12. In an alternative embodiment of the present invention it would be e.g. possible that the bottom part 28 directly functions as fixing aid 18 or 20. In that case e.g. an embodiment could be presented in the form that filter 38 would be connected with the distal surface of bottom part 28, at least partially, e.g. by means of applying an adhesive on it or by means of providing means for hooking, which could reach into the elastic material of filter 38. Thus, fixing aids 18 and 20 could be omitted, whereas fixing aid 20 could still be intended, whereby it would now be arranged in such a way that it can reach into the elastic material of filter 38.

The speaking valve 10 according to FIG. 1 further consists of a cover 46, which features a lower surface 47, onto which filter 38 is attached with its distal end 42 and with its surface 39 at least partially, but preferably fully, e.g. by means of welding, gluing or by means of arranging for respective means for hooking. When an adhesive is intended, it can also just be intended for only a partial section between the distal end 42 with the surface 39 of filter 38 and the lower surface 47 of cover 46, as long as a sufficiently firm grip of cover 46 to filter body 38 can be produced in this way. Cover 46 basically consists of an even plate, which can be made e.g. of a plastic material, which is advantageously relatively hard, but which at the same time features a certain flexibility, in order that it can eventually produce a secure interruption of the air stream in closed position of speaking valve 10. On the distal surface of cover 46, an operating device 60 is arranged approximately in the center, which makes it easier for the patient to find the right pressure point by palpation in order to reach the ideal closing effect for the interruption of the air stream in order to produce a speaking.

Cover 46 features an edge 48 with a lower surface 50. The lower surface 50 can be addressed as ring-shaped area, edge 48 as arranged in a ring-shape.

Filter 38 protrudes beyond end face 24 of housing 12 by approximately 15% of its overall height. If now a patient applies pressure onto cover 46 in the direction of the proximal first opening 14 of housing 12, then filter 38 is compressed, and the lower surface 50 of edge 48 of cover 46 comes into contact with end face 24 as well as the distal surface 25 of enlarging aid 26. Hereby an airstream from the outside of the housing, as it is symbolized e.g. by arrow 64.1, into the inner compartment 11, as well as an airstream in the opposite direction, as it is symbolized by arrow 64.2, is prevented.

In the sense of the present invention, it can e.g. also be possible that there is a central opening in the area of the operating device 60, so that the patient can also breathe air, and air can reach into the inner compartment 11 of housing 12 through this opening, or in opposite direction, that air can also leave the speaking valve through it. By means of the interruption of the airstream due to the contacting of the cover with the housing, speaking is made possible to the patient. FIG. 1 depicts the speaking valve 10 in the initial position, which means in a position, in which the patient is able to breathe, in that air can stream in and also out through a sideways opening 36 and possibly also through a central opening in the area of the operating device 60 that is intended in the cover, into or out of the inner compartment 11 of housing 12. Opening 36 is arranged in a circular-shape all around, without any interruptions.

In order to improve the contacting and thus also the interrupting of the airstream, sealing gaskets 32 or 62 are arranged on the cover piece 46 and at housing 12. Sealing gasket 32 is hereby arranged on the end face 24 of housing 12 as well as on the distal surface 25 of enlarging aid 26. On the respective opposite side there is a sealing gasket 62 on the lower surface 50 of edge 48 of cover 46. Sealing gasket 32 as well as sealing gasket 62 are made of silicone or of another sufficiently soft, that means elastic synthetic material, which is arranged in a medically harmless way.

Figure 2:
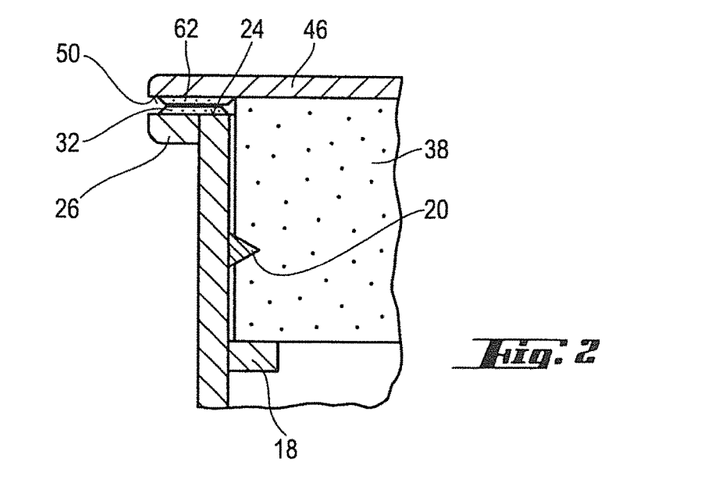
FIG. 2: a detail of the first embodiment of the speaking valve according to the invention according to FIG. 1 in closed position in order to produce a speaking function in cross section.

FIG. 2 depicts the closed position of speaking valve 10 according to FIG. 1 in detail, and hereby in particular the contacting of sealing gasket 32 and 62.

FIG. 3 depicts a bottom view of the first embodiment of speaking valve 10 according to FIG. 1, from which in particular the formation of the bottom part 28 as a three-armed star and its attaching to the inner wall 22 of housing 12 can be seen. The radially symmetrical embodiment of speaking valve 10 can also clearly be derived from FIG. 3, as well as the six fixing aids 20.1, 20.2, 20.3, 20.4, 20.5 and 20.6.

Figure 4:
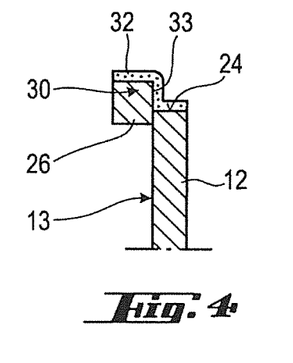
FIG. 4: an enlarged cross sectional depiction of the shaping of the housing wall in the area of the distal end face in a second embodiment of the speaking valve according to the invention.
Figure 5:
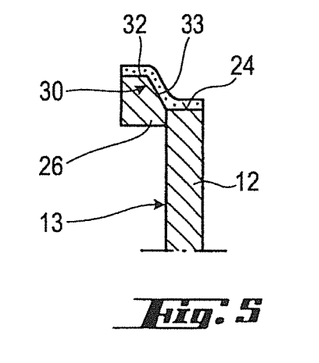
FIG. 5: an enlarged cross sectional depiction of the shaping of the housing wall in the area of the distal end face in a third embodiment of the speaking valve according to the invention.
Figure 6:
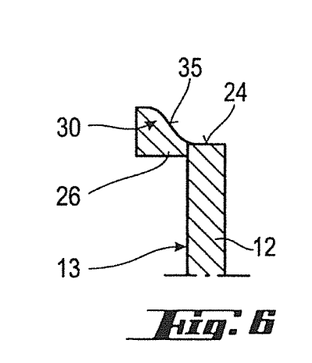
FIG. 6: an enlarged cross sectional depiction of the shaping of the housing wall in the area of the distal end face in a fourth embodiment of the speaking valve according to the invention.

FIG. 4 to FIG. 6 now depict a second, third and fourth embodiment of speaking valve 10 in a detailed depiction concerning the distal end section of housing 12. Hereby, same parts are described with the same reference signs as in the first embodiment according to FIG. 1 to FIG. 3. FIG. 4 depicts a housing 12 with an enlarging aid 26 that is arranged on an outer wall 13 of the housing, which features a first elevation 30. When viewed in cross section, it has a rectangular, almost square shape. On the distal surface of the first elevation 30 and on the end face 24 of housing 12 that was created hereby, a sealing gasket 32 is arranged, whereby the sealing is also arranged on the area between the first elevation 30 and the distal end face 24 of housing 12 within the area of ledge 33 that is arranged there.

FIG. 5 depicts a third embodiment of the speaking valve 10 according to the invention with a housing 12 and an enlarging aid 26 that is arranged on an outer wall 13 of the housing, which features a first elevation 30, whereas in contrast to the second embodiment according to FIG. 4, this one features a sloped ledge 33, which is inclined towards a not really depicted inner compartment 11 of housing 12. The sloped ledge 33 hereby runs from the distal surface of the first elevation 30 downwards to the distal end face 24 of housing 12. A sealing gasket 32 is arranged over the entire surface of the first elevation 30 and of the distal end face 24 of housing 12, which is facing towards the (not depicted) cover 46.

FIG. 6 depicts a fourth embodiment of the speaking valve 10 according to the invention with a housing 12 and an enlarging aid 26 that is arranged on an outer wall 13 of the housing with a first elevation 30. When viewed in cross section, the first elevation 30 features a surface with an almost sigmoidal course of a curved component 35, which is facing towards a not depicted cover 46, which goes over into a distal end face 24 of housing 12.

Figure 7:
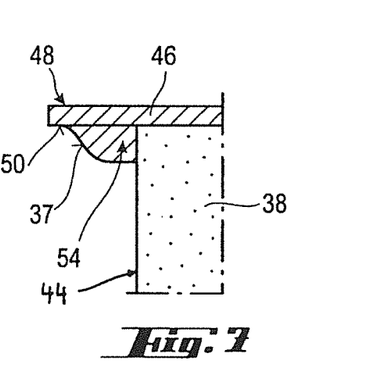
FIG. 7: a cross sectional depiction concerning the shaping of the cover part with an outer contour that has been adapted to the shape of the distal end face of the fourth embodiment according to FIG. 6.

FIG. 7 depicts an embodiment of a cover 46 that is associated to the fourth embodiment of the present invention, with a second elevation 54, which is arranged on a lower surface 50 of edge 48 of cover 46, and which features a curved component 37 when viewed in cross section, with an almost sigmoidal course at least along a partial section of this second elevation 54, whereby there is a more or less even course of this surface close to a filter 38 or of its filter side wall 44, which more or less corresponds to the distal end face 24 of housing 12. FIG. 6 and FIG. 7 illustrate that there is an adaption between the outer contour of the lower surface 50 of cover 46 and that of an outer contour of end face 24 of housing 12 as well as between an outer contour of the first elevation 36 and that of the second elevation 54. Thus, when pressure is applied from the initial position onto cover 46 by the patient, a centering of cover 46 with the filter 38 in housing 12 is accomplished and thus a secure interruption of the airstream in order to accomplish a speaking.

Figure 8:
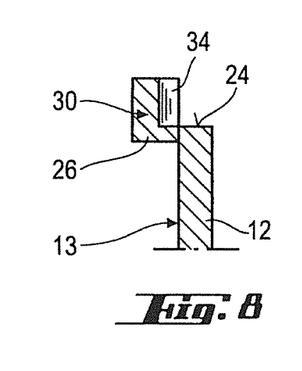
FIG. 8: a cross sectional depiction of an embodiment of the housing with a distal end face with a second centering aid in a fifth embodiment of the speaking valve according to the invention.

FIG. 8 depicts in a fifth embodiment a detailed formation of the distal end section of housing 12 with a distal end face 24 and an enlarging aid 26 that is arranged on an outer wall 13 of the housing 12, which carries a first elevation 30. This first elevation features recesses 34 that are more or less arranged in semicircular shape.

Figure 9:
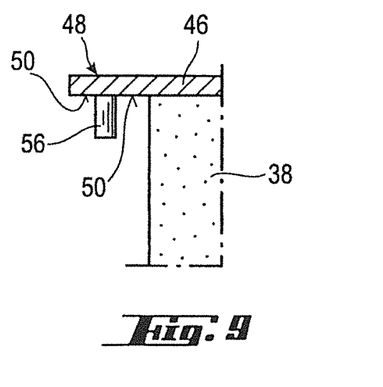
FIG. 9: a cross sectional depiction of the cover part with centering aids that are arranged on the edge in the fifth embodiment of the speaking valve according to the invention corresponding with FIG. 8.

FIG. 9 hereby depicts a complementary arrangement of a cover 46 for this fifth embodiment with a lower surface 50 of edge 48 with pin-like centering aids 56 that are arranged onto it, which can be accommodated by recesses 34 in the distal end section of housing 12.

Figure 10:
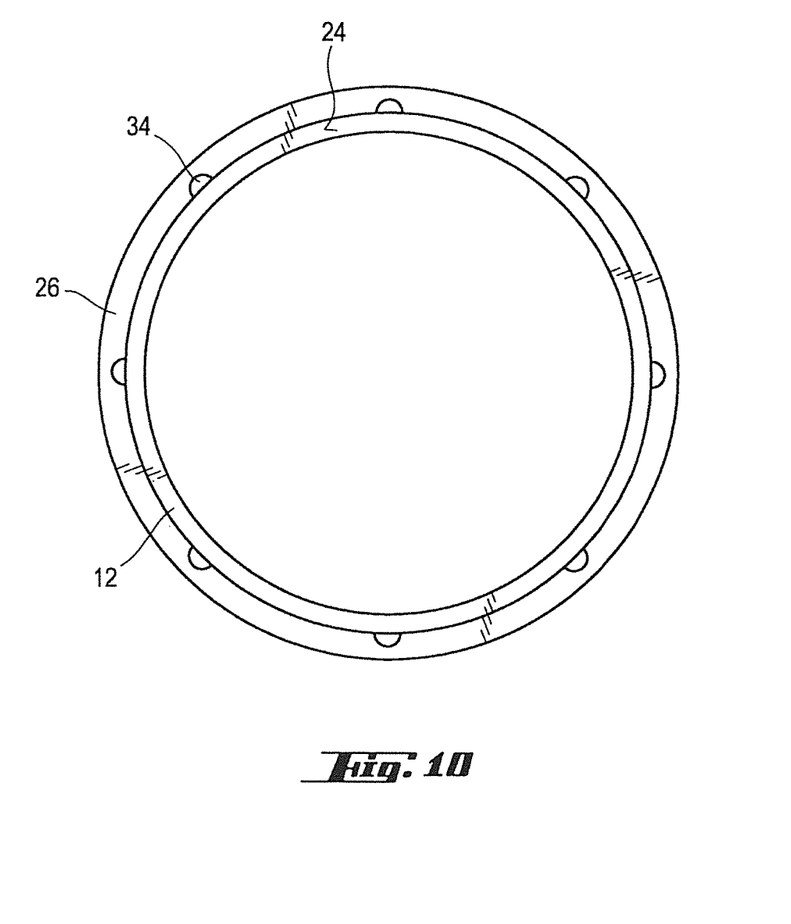
FIG. 10: as well as a top view onto the distal end face of the housing with second centering aids according to the fifth embodiment of the speaking valve according to the invention corresponding with FIG. 8.

FIG. 10 illustrates in a top view onto housing 12 according to FIG. 8, that a total of eight semicircular recesses 34 are intended in the area of the enlarging aid 26 with the first elevation 30, in which a corresponding amount of pin-like centering aids 56, which are arranged onto cover part 46, can be accommodated. The recess 34 can hereby be addressed as the first centering aid in the sense of the present invention, the pin-like centering aid 56 as the second centering aid, whereby the first and the second centering aid work together in order to achieve the centering. The arrangement of first and second centering aids 34 or 56 is also combinable with the formations according to FIG. 4 to FIG. 6 of the second to fourth embodiments, and can of course also be combined with the first embodiment.

In conclusion it should be noted that the formations that are depicted in the figures of the first to the fifth embodiment of the speaking valve according to the invention, are not to be interpreted as limiting or restricting. Rather, the characteristics that are described there can be combined with each other and with the characteristics of the present invention that were described before the figures for further development. Furthermore, it should be noted that the reference signs in the figure descriptions do not limit the scope of protection of the present invention, but that they should merely refer to the embodiments that are depicted in the figures. It may be noted in particular, that the first embodiment that is depicted and described in FIG. 1, can also be arranged in a different way, and that in particular the bottom part 28 can also function as fixing aid 18 or 20, so that eventually also a reduction of the construction height of the speaking valve according to the invention can be accomplished.

The invention claimed is:

1. A speaking valve for laryngectomized and tracheotomized persons with a housing with a proximal first opening and a distal second opening, a filter which is at least partially surrounded by the housing, which filter is made of an elastic material, with a proximal first end and a distal second end, wherein the filter partially protrudes beyond an end face of the housing at the distal second opening, the housing having at least one flange extending outwardly from an outer wall of the housing to act as an enlarging aid and wherein a cover is connected by means of at least one partial region of its bottom surface to an upper side of the filter at its distal second end, whereby a diameter $d_1$ of the cover is greater than a diameter $d_2$ of the filter, so that an edge is formed that is protruding beyond a lateral filter wall of the filter, wherein by application of pressure onto the cover from an initial position, a lower surface of the edge of the cover at least partially interacts with the end face and the flange of the housing in order to produce a closed position of the speaking valve, and wherein the cover together with the filter returns to the initial position when unloaded.

2. The speaking valve according to claim 1 wherein the filter is held by a fixing aid on an inside wall of the housing, the fixing aid being arranged at some distance to the proximal first opening of the housing.

3. The speaking valve according to claim 2 wherein the fixing aid is at least partially arranged as a circulating flange, in the shape of a ridge and/or in a way of a ledge that is reducing particularly towards the center of the housing.

4. The speaking valve according to claim 1 wherein the housing consists of an air permeable bottom part that is arranged at the proximal first opening.

5. The speaking valve according to claim 1 wherein the cover is attached to the filter in a solid or detachable manner.

6. The speaking valve according to claim 4 wherein the cover and the filter are glued, welded or hooked together.

7. The speaking valve according to claim 1 wherein the at least one flange is circular.

8. The speaking valve according to claim 1 wherein an outer contour of the lower surface of the edge of the cover and an outer contour of the end face of the housing and/or of the flange are adapted in such a way, that they fit into each other.

9. The speaking valve according to claim 1 wherein a first elevation is arranged on the end face and/or on the at least one flange.

10. The speaking valve according to claim 1 wherein a second elevation is arranged on a lower surface of the edge of the cover.

11. The speaking valve according to claim 1 wherein at least one centering aid is arranged on the lower surface of the edge of the cover and/or of the end face or on the at least one flange of the housing.

12. The speaking valve according to claim 1 wherein at least a partial sealing gasket is arranged on the lower surface of the edge of the cover, and/or the end face or the at least one flange.

13. The speaking valve according to claim 12 wherein the sealing gasket is produced in one piece together with the housing or cover.

* * * * *